(12) United States Patent
Takata et al.

(10) Patent No.: US 6,813,338 B2
(45) Date of Patent: Nov. 2, 2004

(54) METHOD FOR MEASURING POWDER X-RAY DIFFRACTION DATA USING ONE-OR-TWO-DIMENSIONAL DETECTOR

(75) Inventors: Masaki Takata, Hyogo (JP); Eiji Nishibori, Hyogo (JP); Makoto Sakata, Hyogo (JP); Jimpei Harada, Hyogo (JP)

(73) Assignees: Japan Synchrotron Radiation Research Institute, Sayo-gun (JP); Rigaku Corporation, Akishima (JP); Riken, Wako (JP)

( * ) Notice: Subject to any disclaimer, the term of this patent is extended or adjusted under 35 U.S.C. 154(b) by 186 days.

(21) Appl. No.: 10/291,427

(22) Filed: Nov. 12, 2002

(65) Prior Publication Data

US 2003/0091147 A1 May 15, 2003

(30) Foreign Application Priority Data

Nov. 13, 2001 (JP) .......................... 2001-347637

(51) Int. Cl.[7] .......................................... G01N 23/207
(52) U.S. Cl. ............................ 378/75; 378/70; 378/71
(58) Field of Search .............................. 378/70, 71, 75, 378/82, 86

(56) References Cited

U.S. PATENT DOCUMENTS

| 4,991,191 A | | 2/1991 | Suryanarayanan | |
| 6,064,717 A | * | 5/2000 | Ortega et al. | 378/71 |
| 6,744,850 B2 | * | 6/2004 | Fanton et al. | 378/83 |

FOREIGN PATENT DOCUMENTS

| JP | 04372892 | 12/1992 |
| JP | 11051881 | 2/1999 |

OTHER PUBLICATIONS

M. Beno, et al., "Application on New Synchrotron Powder Diffraction Techniques to Anomalous Scattering From Glasses", Review of Scientific Instruments, American Institute of Physics. New Yor, U.S. vol. 66, No. 2, part 2, Feb. 1, 1995, pp. 1308–1310.

J. Chrosch, et al., "High–Resolution X–Ray Diffraction Analysis of Magnetically Aligned High–$T_c$ Superconducting Ceramics", Physica C, North–Holland Publishing Amsterdam, NL, vol. 265, No. 3–4 Jul. 10, 1996, pp. 233–242.

Partial European Search Report dated Mar. 17, 2003.

A.L. Ortiz, et al., "Quantitative polytype–composition analyses of SiC using X–ray diffraction: a critical comparison between the polymorphic and the Rietveld Methods," Journal of the European Ceramic Society 21 (2001) pp. 1237–1248.

A.L. Ortiz, et al., "X–ray powder diffraction analysis of a silicon carbide–based ceramic," Materials Letters 49 (2001) pp. 137–145.

* cited by examiner

Primary Examiner—Edward J. Glick
Assistant Examiner—Elizabeth Keaney
(74) Attorney, Agent, or Firm—Banner & Witcoff, Ltd.

(57) ABSTRACT

High-resolution powder diffraction is performed using high-energy synchrotron radiation as an x-ray source in such a way that a detector mounted on a measuring instrument such as a diffractometer is moved by smaller distances than the distance between adjacent x-ray detection units (pixels) in order to measure data for interpolation between pixels and the obtained interpolating data are put together to thereby improve the spatial resolution in measurement that has been limited by the detection unit in the detector.

6 Claims, 6 Drawing Sheets

SCHEMATIC REPRESENTATION OF MEASUREMENT WITH DATA INTERPOLATION

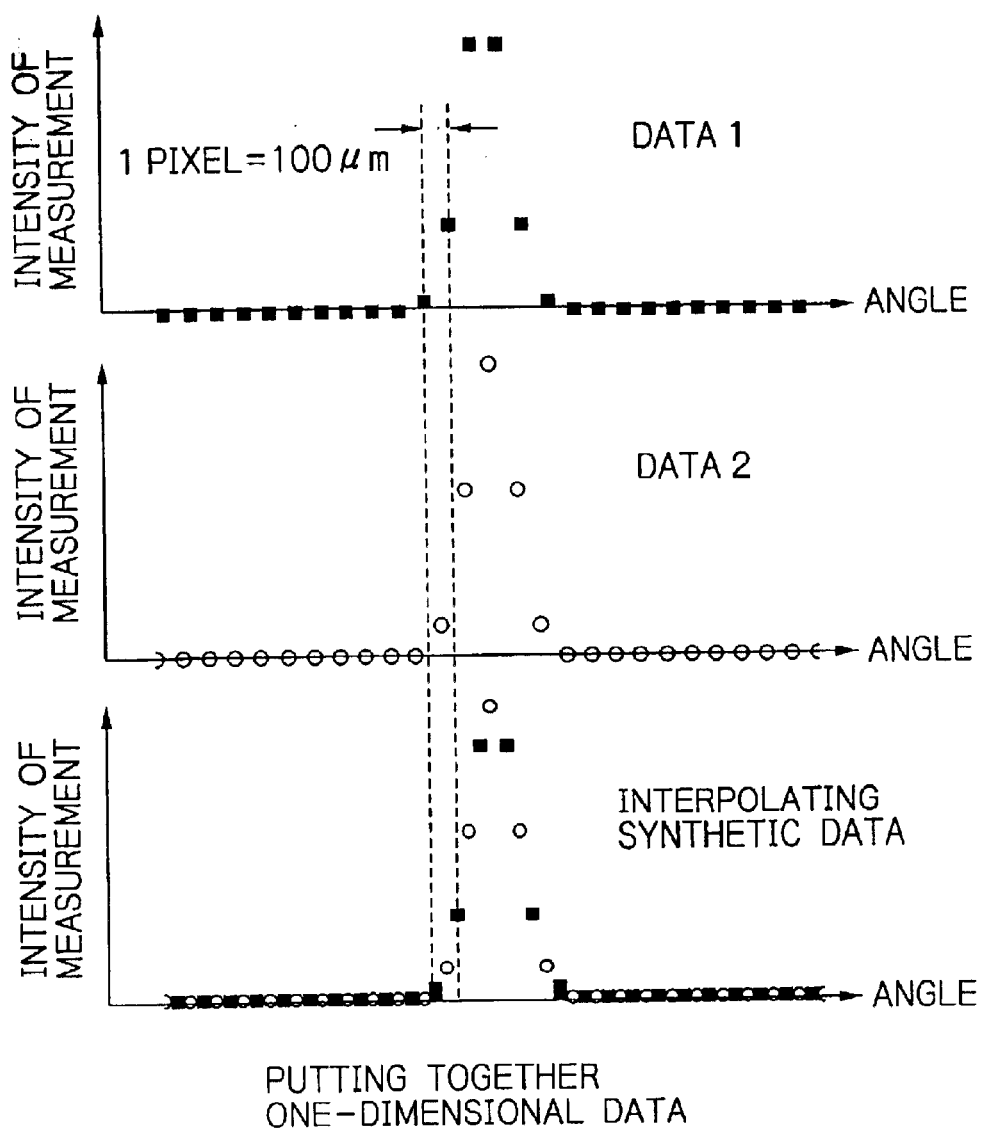

SCALING OF INTENSITY

RESULT OF DATA SYNTHESIS

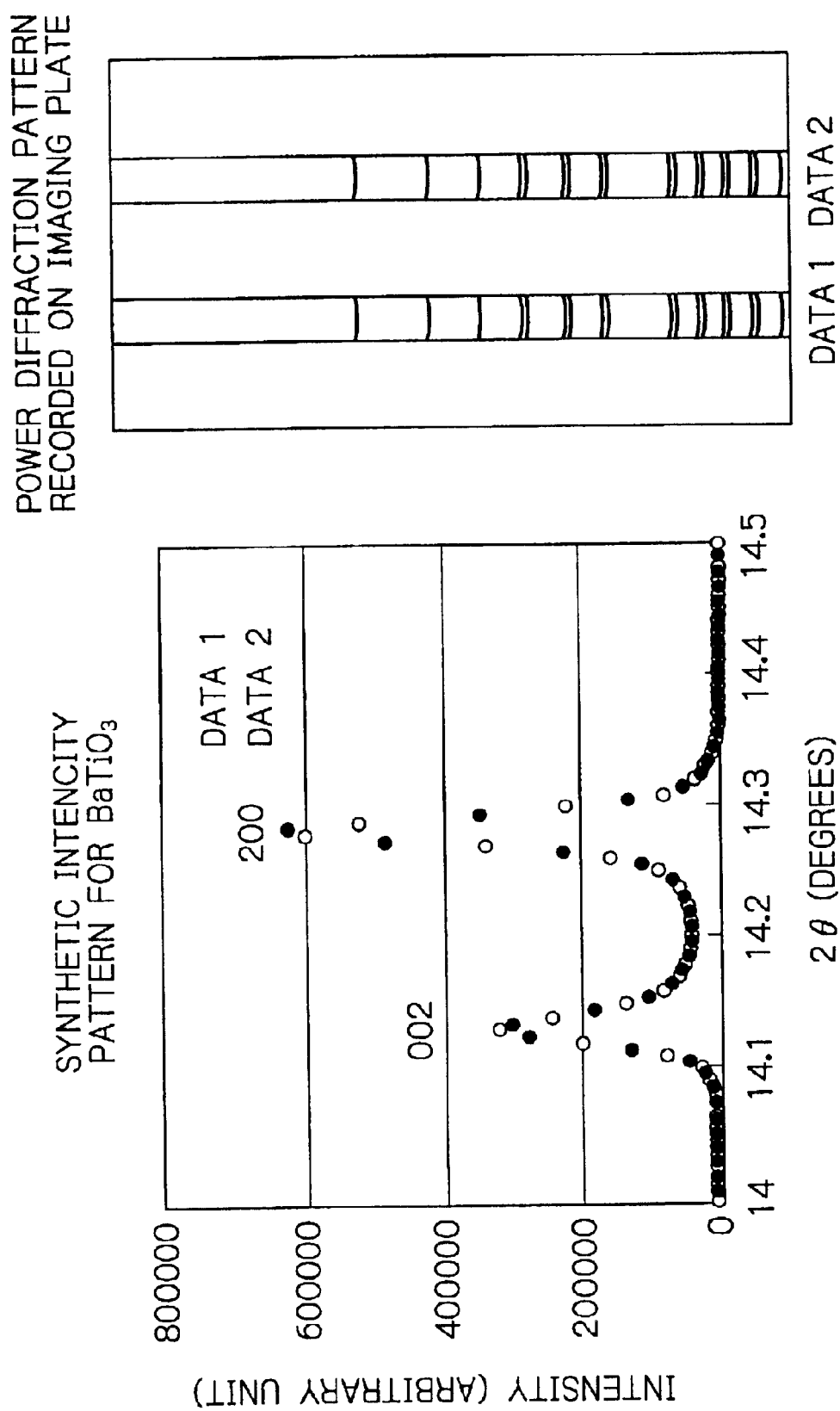

*Fig. 5A* PRIOR ART
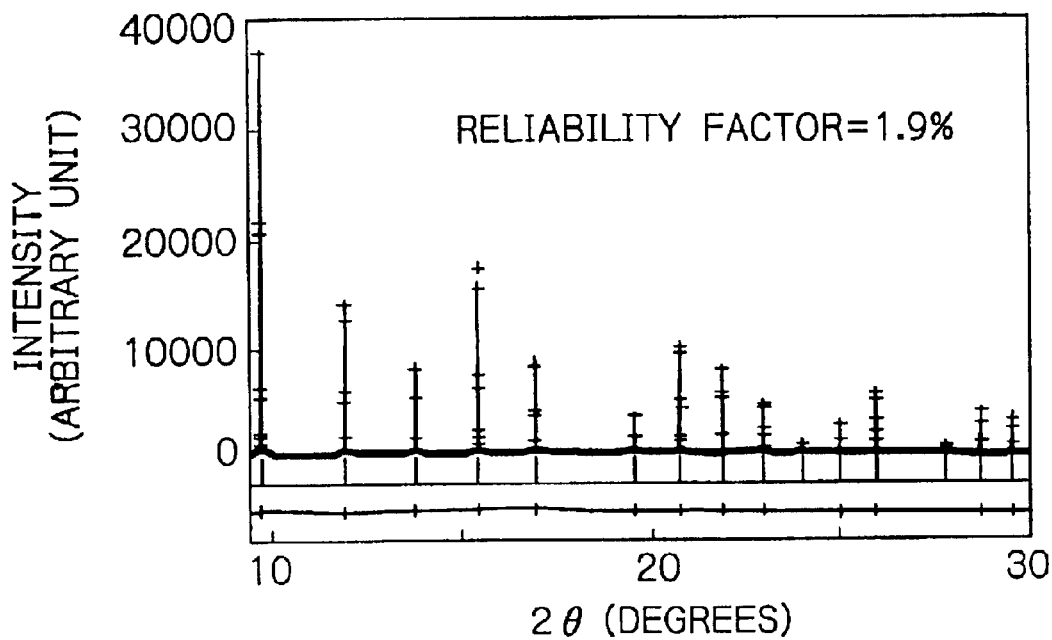
*Fig. 5B* INVENTION
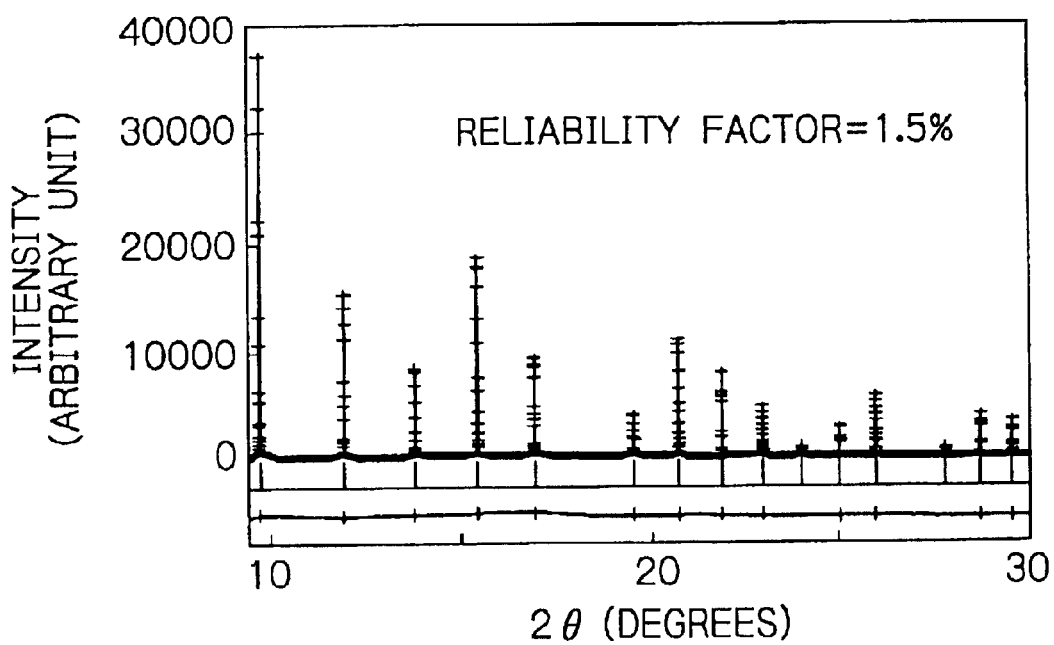

SCHEMATIC REPRESENTATION OF
MEASUREMENT WITH DATA INTERPOLATION

METHOD FOR MEASURING POWDER X-RAY DIFFRACTION DATA USING ONE-OR-TWO-DIMENSIONAL DETECTOR

This application is based upon and claims the benefit of priority from Japanese Patent Application No. 2001-347637, filed Nov. 13, 2001, the entire contents of this application are incorporated herein by reference.

BACKGROUND OF THE INVENTION

This invention finds industrial applicability in measuring x-ray and synchrotron radiation powder diffraction data using one- and two-dimensional detectors such as a position sensitive proportional counter (PSPC), an imaging plate and a large CCD detector.

An essential problem that should be addressed in measuring powder x-ray diffraction data is how to achieve efficient improvement in the angular resolution and the statistical precision of data. One means for solving the problem of statistical precision is using a one- or two-dimensional detector. This not only shortens the time required to measure the whole powder diffraction data; in addition, the time for measurement at an individual point is equal to the time for measuring the whole powder diffraction data and, hence, the overall time of measurement can be shortened by a factor of at least 10, enabling a marked improvement in statistical precision to be realized efficiently.

For improvement of angular resolution, it is effective to perform a parallel-beam x-ray diffraction experiment using a highly directional x-ray source such as synchrotron radiation. On the other hand, the effort to improve the angular resolution of data is limited by the position resolution of the detector, or the size of a detection unit. For example, it is impossible to get information finer than a data detection unit (pixel) in the detector such as an imaging plate. Hence, in order to measure finer (higher-resolution) data, various efforts have been made to reduce the actual size of the detection unit or improve the apparent resolution of the detection unit by increasing the size of a measuring instrument such as a diffractometer on which the detector is to be mounted.

Angular resolution is the resolution of a diffraction angle in x-ray diffraction data and high angular resolution means a small half-peak width of powder x-ray profile (which is the width at half intensity as expressed by diffraction angle). Angular resolution is expressed in degrees.

The imaging plate is a new x-ray film prepared by coating a plastic film with a stimulable phosphor that serves as a memory of x-ray energy. Unlike PSPC and CCD that perform measurement with sensing elements that are fixed in absolute positions on the detector, the imaging plate is capable of detecting x-rays in a desired position on the film (20 cm×40 cm) and the detection unit can be set in any desired position. In addition, the imaging plate has high sensitivity and wide exposure latitude. Because of these advantages, the imaging plate is currently one of the most commonly used two-dimensional detectors.

The following may be mentioned about the measurement of x-ray diffraction data using the imaging plate.

(1) At the beginning of 1990, the size of a pixel as the detection unit was 100 $\mu$m square. Later technological development reduced the pixel size to 50 $\mu$m square and even to 25 $\mu$m square. However, the resolution of silver halide films is about 10 $\mu$m square and it will be many years before this level is achieved by the imaging plate.

(2) The apparent resolution can be improved by increasing the size of the diffractometer on which the imaging plate is to be mounted and thereby increasing the distance of measurement. However, if the distance of measurement is doubled, the resolution can only be increased by a factor of two; in other words, a bigger diffractometer does not achieve an outstanding improvement in resolution.

(3) With the advent of an x-ray source having ultra-high resolution such as synchrotron radiation, there has been a growing demand to improve the resolving power of the detector.

Thus, a new approach has been desired in order to improve the resolution in measurement of x-ray diffraction data using a one- or two-dimensional detector.

A prior art technology for providing improved position resolution in measurement with a one- or two-dimensional detector is a radiation imaging device for typical use in x-ray medical equipment that is designed to obtain two-dimensional image data by displacing a two-dimensional array sensor in both a horizontal and a vertical direction by a distance equal to one half the pixel width (Japanese Patent Laid-Open No. 372892/1992).

Similar prior art techniques include the following: a mask is placed before a two-dimensional detector that is smaller than the detection unit and moved relative to the detector relative so as to provide a fine two-dimensional image (Japanese Patent Laid-Open No. 82305/1994); a two-dimensional detector is moved by small distances in an imaging device in an x-ray interferometer to produce composite imaging data and the detection efficiency of each sensing element is corrected to enhance the space resolution (Japanese Patent Laid-Open No. 51881/1999); and a one-dimensional x-ray detector is moved by small distances to produce a fine two-dimensional image (Japanese Patent Laid-Open No. 10220/1989).

There are two other techniques based on a similar concept. In one approach, a detector array consisting of multiple one-dimensional rows of radiation sensing elements is moved in a predetermined direction as the output data from each element is gathered by a photon counting method so as to capture a two-dimensional radiation image (Japanese Patent Laid-Open No. 204283/1992); the other approach is a radiation CT apparatus which allows an object to be exposed to a radiation such as x-rays or $\gamma$-rays at a fan beam angle and in which the step of translating the radiation source and the detector relative to each other and the step of rotating the detector about the object are repeated by turns to reconstruct slices through the object to produce a tomogram (Japanese Patent Laid-Open No. 201253/1990).

As described above, various apparatuses and methods have been proposed with a view to improving resolution in x-ray imaging using a one- or two-dimensional detector. However, in order to apply those techniques to measurement of powder x-ray diffraction data, the following problems must be solved.

(1) Synchrotron radiation from an accelerator is x-rays which are unstable in incident strength and subject to variations. Since measurement of x-ray diffraction data using such unstable x-rays involves variations in the intensity of measurement, the prior art techniques are not capable of efficient data synthesis and fail to function properly.

(2) If highly directional parallel-beam x-rays such as synchrotron radiation are employed to measure ultrahigh resolution and complexly shaped diffraction data, the prior art involving the correction of shape and detection efficiency of sensing elements (Japanese Patent Laid- Open No. 51881/1999) is so strongly correlated to the problem of 1) that consistency in data correction is not guaranteed.

SUMMARY OF THE INVENTION

An object, therefore, of the present invention is to improve the angular resolution in the measurement of x-ray powder diffraction data with a one- or two-dimensional detector to thereby ensure that the aforementioned problems with employing parallel-beam x-rays such as synchrotron radiation that inherently undergo attenuation of incident strength over time and which are highly directional are solved while permitting powder diffraction data of high angular resolution to be measured in high precision using a one- or two-dimensional detector.

In the conventional methods of measuring powder x-ray diffraction data, a one-dimensional detector (PSPC) or a two-dimensional detector (imaging plate, IP) remains fixed or is moved during data measurement. According to the invention, a high-resolution powder diffraction experiment is performed using synchrotron radiation or other highly directional, parallel-beam x-rays as an x-ray source in such a way that a detector mounted on a measuring instrument such as a diffractometer is finely moved by distances smaller than the distance between adjacent x-ray detection units (pixels) in order to measure data for interpolation between pixels and the obtained interpolating data are put together to thereby improve the spatial resolution in measurement that has been limited by the detection unit in the detector (i.e., the fineness of each pixel in the imaging plate). This can theoretically improve resolution without increasing the size of the measuring instrument or decreasing the size of the detector.

The idea of the present invention which relies upon detector movement for improving spatial resolution finds a lot of parallels in the prior art. What is unique about the invention is that it solved the first problem of the prior art by synthesizing final powder diffraction data with individual pieces of data being scaled on the basis of their background intensities. By this technology of the invention, variations in the intensity of synchrotron radiation as x-rays can be corrected simultaneously with the synthesis of data. In the method of the invention, scaling the intensity of measurement for two kinds of data on the basis of the averages of their background intensities is an indispensable step and particularly effective in an experiment using synchrotron radiation from an accelerator as an x-ray source which inherently experiences intensity attenuation over time.

By employing a large detector such as an imaging plate, measurement can be performed over a very wide area (20 cm×40 cm) at a time with the detection unit being set in a desired position. In addition, by using a two-dimensional detector that does not require the correction of detection efficiency, data synthesis can be accomplished without correcting the shape or detection efficiency of sensing elements. This contributes to solving the second problem of the prior art.

As for the improvement in statistical precision that can be achieved with a two-dimensional detector, data in a direction perpendicular to the direction of detector movement are integrated over a few pixels to construct one-dimensional powder diffraction data and, as a result, the statistical precision of data is improved by a degree corresponding to the number of pixels over which integration was made. When a two-dimensional detector is to be used in the invention, it is particularly noteworthy that a train of data in a direction perpendicular to the direction of data synthesis may be integrated over a few pixels to an extent that will not deteriorate the resolution of powder diffraction profiles but which is sufficient to improve the statistical precision of intensity. This technique has no parallel in the prior art.

BRIEF DESCRIPTION OF THE DRAWINGS

FIG. 1 shows results of measuring intensity distribution by applying the method of the invention to a one-dimensional detector;

FIG. 3 shows x-ray diffraction intensity profiles obtained at BL02B2 of SPring-8, a large synchrotron radiation factory, by applying the method of the invention to an x-ray powder diffraction experiment;

FIG. 5A shows the reliability factor in crystal's structure determination by analyzing the data of measurement in accordance with the prior art by the Rietveld method which is a common technique for powder x-ray structural analysis;

FIG. 5B shows the reliability factor in crystal's structure determination by analyzing the data of measurement in accordance with the present invention by the Rietveld method.

DETAILED DESCRIPTION OF THE INVENTION

The present invention is now described in greater detail by reference to the following examples which are intended for illustrative purposes only.

EXAMPLE 1

FIG. 1 shows schematically an example of applying the method of data synthesis of the invention to measurements with a one-dimensional detector. The measurement was directed to an intensity distribution having a Gaussian distribution. In the example, the size of a minimum detection unit (pixel) in the detector was 100 $\mu$m square and the angular resolution in measurement of diffraction data is expressed by the angle subtended by a source of signal transmission having the intensity distribution of interest.

(1) The graph labeled "data 1" shows the result of an ordinary measurement with the detector fixed. The size of a minimum detection unit is the detection limit, or resolution. The horizontal axis plots angular resolution which is expressed by 100/a ($\mu$rad), in which a represents the distance from the source of signal transmission. Since the intensity distribution is narrower than angular resolution, one can readily see that no reliable intensity distribution profile can be obtained with solid squares (■)alone.

(2) In order to obtain data for interpolation between two pixels, the diffractometer carrying the detector was precisely moved with a stepping motor or the like to measure data 2 (●).

(3) By putting together measured data 1 and 2, interpolating synthetic data could be obtained as shown in the graph at the bottom of FIG. 1. The obtained intensity profile distinctly had a Gaussian distribution.

EXAMPLE 2

Figure 2A:
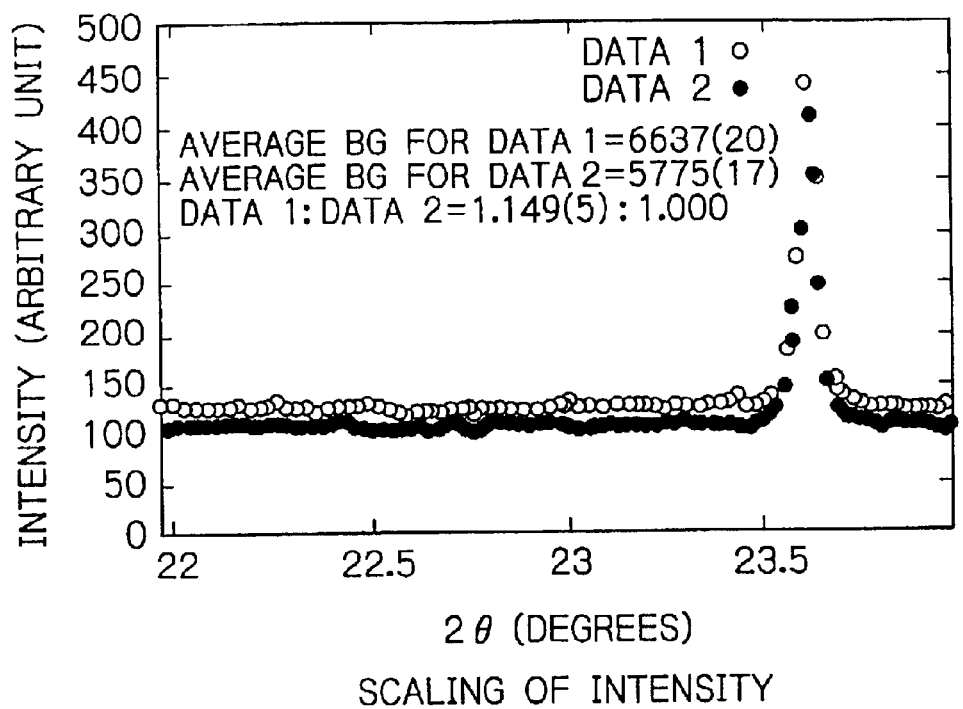
FIG. 2A shows scaled data 1 and 2 that were yet to be put together.
Figure 2B:
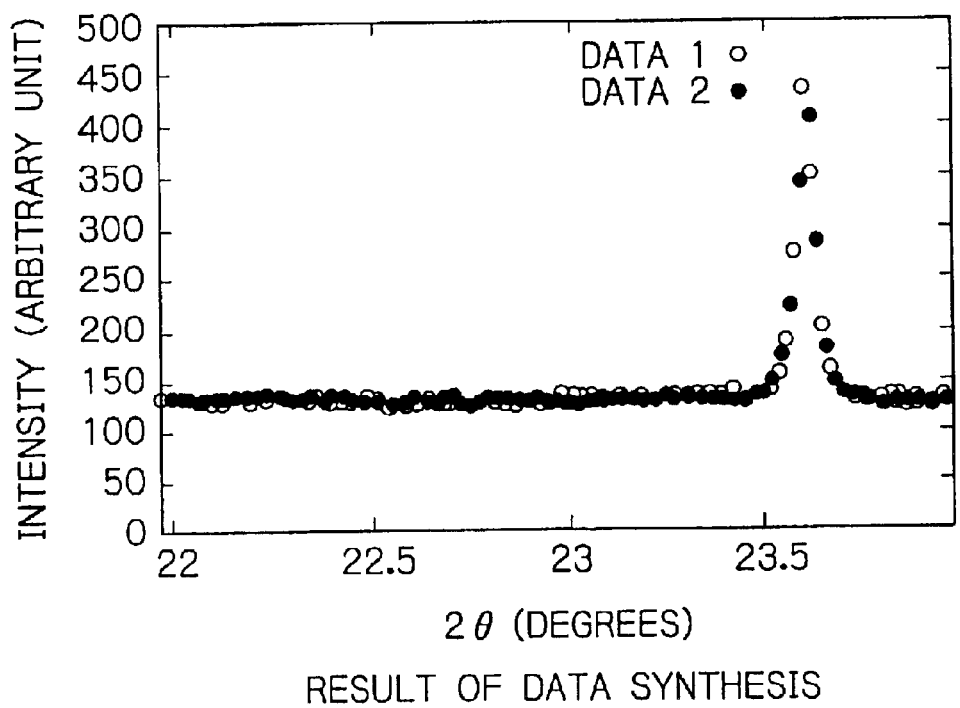
FIG. 2B shows the result of putting together scaled data 1 and 2.

When synchrotron radiation data was used, the intensity of incident x-rays attenuated and two kinds of diffraction intensity data, which underwent relative changes as shown in FIG. 2A, could not be put together in the correct way. In that case, the intensity ratio between data 1 and data 2 was calculated from the mean background intensities in relatively flat portions of curves which should theoretically be identical between the two kinds of data. By scaling the intensity data with the calculated ratio which was 1.149:1.000 in the illustrated case, data 1 and data 2 could be put together with the variations in the intensity data for the incident x-rays being properly corrected as shown in FIG. 2B. This is a very unique feature of the method of the invention.

EXAMPLE 3

FIG. 3 shows the result obtained when the method of Example 2 was actually applied to an x-ray powder diffraction experiment at SPring-8, BL02B2. The size of pixels in the detector was 50 μm square. Obviously, data 1 effectively interpolated data 2 and vice versa so that a profile of x-ray diffraction intensity could be closely measured by the concept of the invention.

EXAMPLE 4

Figure 4A:
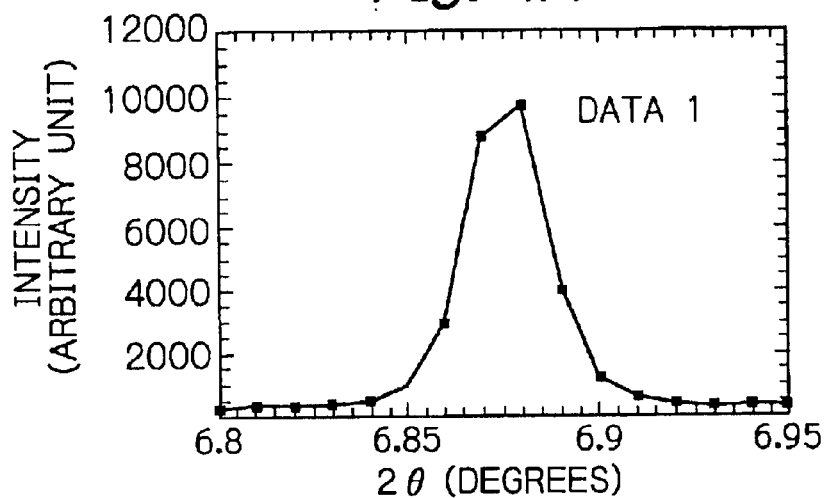
FIGS. 4A, 4B and 4C show the intensities of diffracted x-rays as obtained by applying the method of the invention to a powder x-ray diffraction experiment on $LaB_6$ at SPring-8, BL02B2.
Figure 4B:
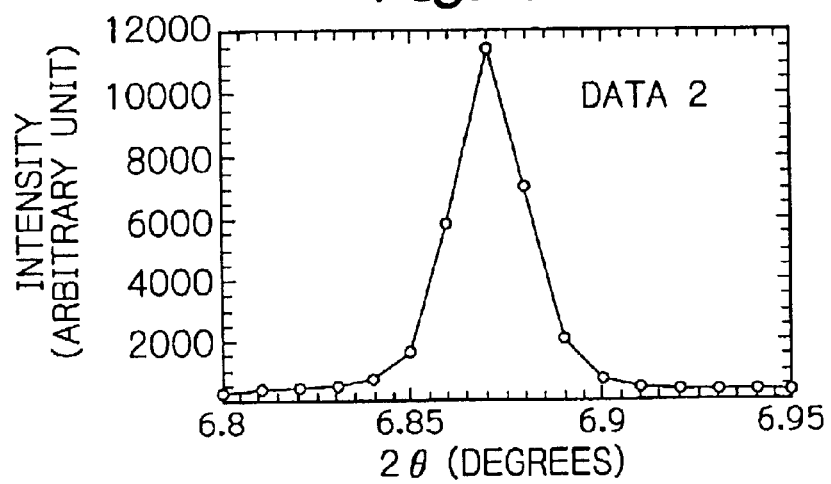
Figure 4C:
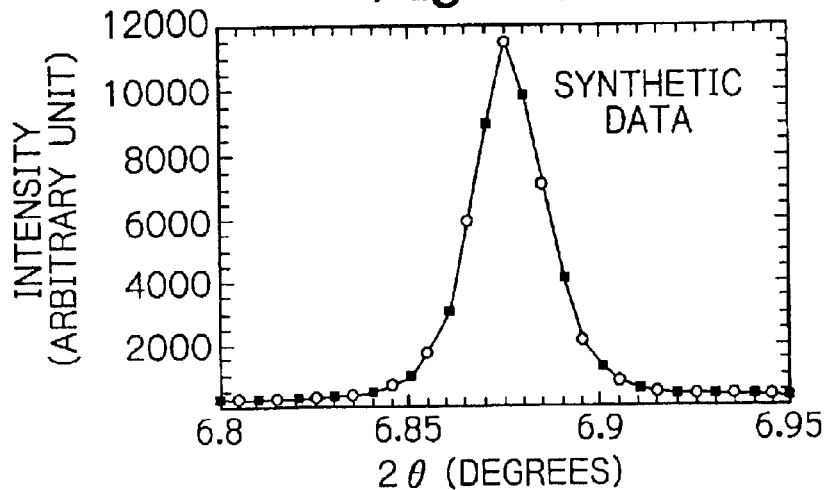

FIGS. 4A–4C show results of applying the method of the invention to a powder x-ray diffraction experiment at SPring-8, BL02B2. The sample was Standard Reference Material 660, a $LaB_6$ sample prepared at NIST (the National Institute of Standards & Technology), and an imaging plate was used as a detector. The respective points of data in FIGS. 4A–4C represent the intensity of diffracted x-rays as measured with corresponding pixels. By using the invention technique of raising the statistical precision, intensity was integrated over 50 pixels in the direction of pixel arrangement which is perpendicular to the paper; this achieved a 50-fold increase in intensity.

In the first place, a diffraction profile was measured with the imaging plate fixed and this gave data 1 (FIG. 4A). Then, the imaging plate was moved by a distance equal to one half the pixel size and a diffraction profile was measured to give data 2 (FIG. 4B). Obviously, no neat diffraction profile could be measured for data 1 or data 2 by the conventional technique.

FIG. 4C shows the synthetic data measured by the method of the invention and the shape of a diffraction profile is represented in detail, clearly demonstrating the effectiveness of the invention which was already illustrated in FIG. 1. In structural analysis by powder x-ray diffraction, the area represented by the profile shown in FIG. 4C provides the integral reflection intensity necessary for crystal structure determination. Therefore, the present invention provides an important technique for measuring the correct integral reflection intensity, namely, for determining the correct crystal structure.

EXAMPLE 5

Rietveld analysis which was a common method of structural analysis by powder x-ray diffraction was performed on both data of measurement that had been subjected to data synthesis and data of measurement that had been subjected to data synthesis by the invention; the results are shown in FIGS. 5A and 5B, respectively. The reliability factor in structural analysis is expressed by $100 \times |I_{oal} - I_{obs}|/I_{obs}$, where $I_{obs}$ is an integral reflection intensity and $I_{oal}$ is the intensity calculated from a crystal's structure model. The reliability factor is an index for the agreement between the observed intensity and the calculated intensity. Without data synthesis, the reliability factor ($R_1$) in the determined crystal structure was 1.9% whereas the data of measurement obtained by the invention had $R_1 = 1.5\%$.

The crystal structure of $LaB_6$ used as the reference sample is well known and the lower the value of reliability factor, the higher the reliability of the intensity data obtained. If the reliability factor in a structural analysis of the reference sample decreases from 1.9% to 1.5%, the improvement is about 20% which is an outstanding value in terms of analytical precision. It is therefore clear that the invention contributes a lot to improving the resolution and reliability in the measurement of powder x-ray diffraction data.

EXAMPLE 6

Figure 6:
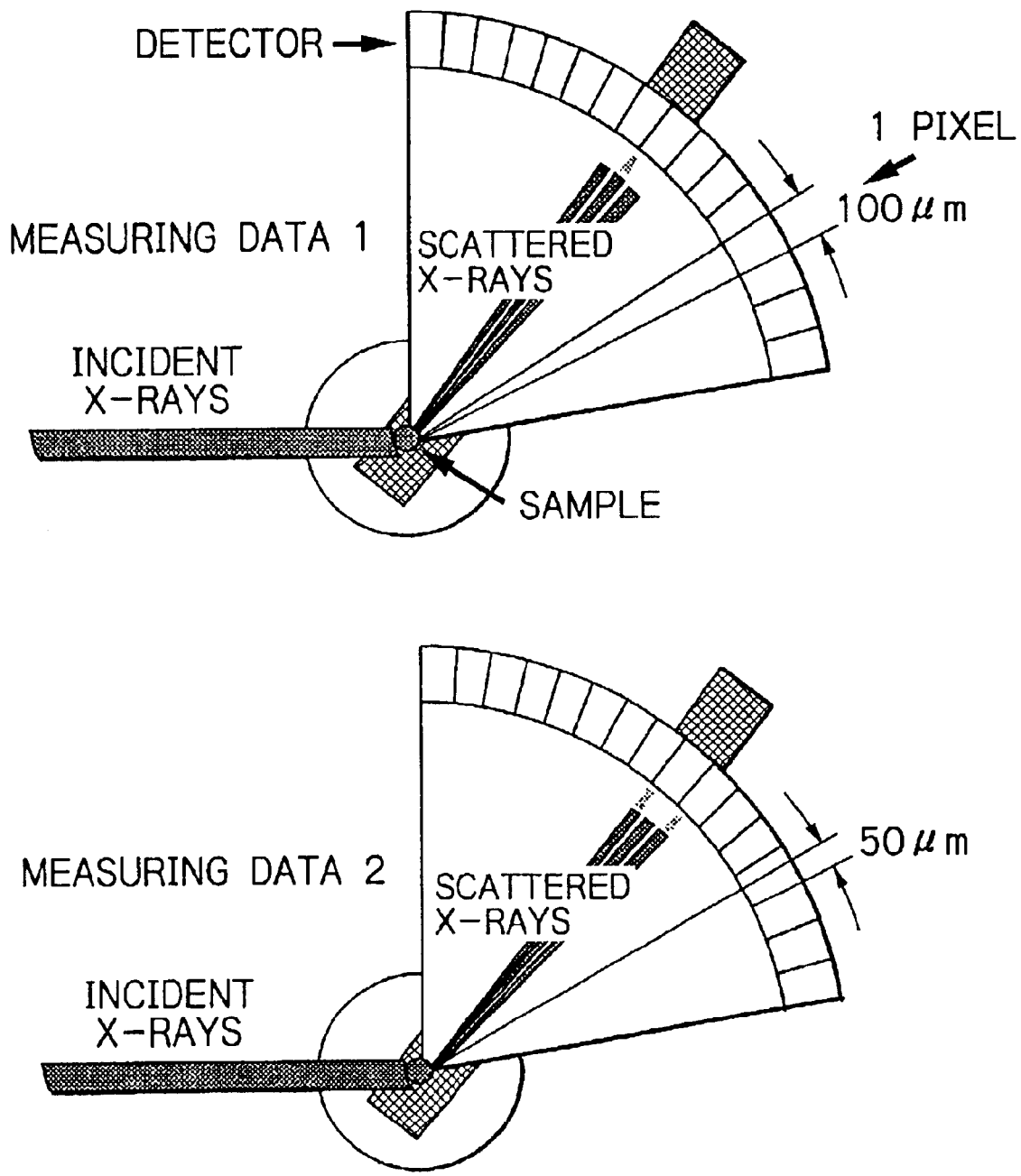
FIG. 6 shows an apparatus for implementing the method of measurement according to the invention.

FIG. 6 shows schematically an apparatus for performing measurement by the method of the invention using either an imaging plate or a curved PSPC as a detector. The size of each detection unit is supposed to be 100 μm. The detector measures scattered x-rays from the sample with respective detection units. After data 1 is measured, the curved detector is rotated around the sample such that each detection unit is displaced by 50 μm. A second measurement is performed to obtain data 2, which is subsequently composited with data 1. Depending on the object, the detector may be planar rather than curved but processing is still the same.

In the upper part of FIG. 6, x-rays at both ends strike two pixels and can be measured but the center ray is not measured since it falls in the gap between the two pixels. In the lower part of FIG. 6, each pixel is displaced by a distance equal to one half its size, so the center x-ray hits a pixel to be measured but the two rays at both ends fall in inter-pixel gaps and are not measured.

In order to measure the diffraction of x-rays with unstable intensity such as synchrotron radiation by the method of the invention, a detector mounted on the measuring instrument is finely moved by one nth (1/n) of the distance between adjacent x-ray detection units (pixels) and data for interpolation between pixels is measured n times so that the variation in incident intensity is corrected by using part of the obtained data and then the measured data are put together to ensure that the spatial resolution of measurement that has been limited by the detection unit in the detector is improved by a factor of n; this is a characteristic, marked advantage of the invention.

The present invention can also improve resolution without increasing the size of the measuring instrument or decreasing the size of the detection unit. When a two-dimensional detector is to be used in the invention, data in a direction perpendicular to the direction of detector movement may be integrated over a few pixels to construct one-dimensional powder diffraction data and, as a result, the statistical precision of data is improved by a degree corresponding to the number of pixels over which integration was made. This is another characteristic, marked advantage of the invention.

What is claimed is:

1. A method for measuring high-resolution powder x-ray diffraction data with a one- or two-dimensional detector using highly directional parallel-beam x-rays as a radiation source, wherein the detector mounted on a measuring instrument is finely moved by uniform distances which are obtained by dividing the distance between adjacent x-ray detection units (pixels) by a desired number n so as to measure data for interpolation between pixels on the basis of division by n and n kinds of data obtained before and after the movement of the detector are put together to achieve n-fold improvement in the spatial resolution in measurement that has been limited by the detection unit in the detector.

2. The method according to claim 1 wherein n is an integer of 1–10.

3. A method for measuring high-resolution powder x-ray diffraction data with a one- or two-dimensional detector using highly directional parallel-beam synchrotron radiation as a source of x-rays, wherein the detector positioned mounted on a measuring instrument is finely moved by uniform distances which are obtained by dividing the distance between adjacent x-ray detection units (pixels) by a desired number n so as to measure data for interpolation between pixels on the basis of division by n and in order to compensate for the relative changes in intensity data on account of the attenuation of incident synchrotron radiation that occurs when the respective data are put together, the ratio in the intensity of measurement between data is calculated from the average intensities of measurement in relatively flat portions of background intensities of the detected data and the intensities of measurement are scaled by the calculated ratio to produce synthetic data, thereby achieving n-fold improvement in the spatial resolution in measurement that has been limited by the detection unit in the detector.

4. The method according to claim 3 wherein n is an integer of 1–10.

5. A method for measuring high-resolution powder x-ray diffraction data with a one- or two-dimensional detector using highly directional parallel-beam synchrotron radiation as a source of x-rays, wherein said detector mounted on a measuring instrument is finely moved by uniform distances which are obtained by dividing the distance between adjacent x-ray detection units by a desired number n so as to measure data for interpolation between pixels on the basis of division by n and when those data are put together, a train of data in a direction perpendicular to the direction of data synthesis is integrated over a few pixels to such a degree that the resolution of a powder diffraction profile will not be deteriorated, whereby the statistical precision of intensity is improved to achieve n-fold improvement in the spatial resolution in measurement that has been limited by the detection unit in the detector.

6. The method according to claim 5 wherein n is an integer of 1–10.

* * * * *

UNITED STATES PATENT AND TRADEMARK OFFICE
CERTIFICATE OF CORRECTION

PATENT NO. : 6,813,338 B2
DATED: : November 2, 2004
INVENTOR(S): : Masaki Takata et al.

It is certified that error appears in the above-identified patent and that said Letters Patent is hereby corrected as shown below:

<u>Column 8,</u>
Line 10, replace "units by" with -- units (pixels) by --

Signed and Sealed this

Second Day of August, 2005

JON W. DUDAS
*Director of the United States Patent and Trademark Office*